United States Patent [19]

Kubota et al.

[11] 4,186,151

[45] Jan. 29, 1980

[54] PROCESS FOR PREPARING A 5,5'-METHYLENEBIS(2-HYDROXY-4-ALKOXYBENZOPHENONE)

[75] Inventors: Naohiro Kubota; Toshihiro Shibata, both of Urawa; Kazuo Sugibuchi, Tokyo, all of Japan

[73] Assignee: Argus Chemical Corporation, Brooklyn, N.Y.

[21] Appl. No.: 880,295

[22] Filed: Feb. 22, 1978

[51] Int. Cl.$^2$ .................................... C07C 45/00
[52] U.S. Cl. .................... 260/591; 260/45.8 N; 260/45.8 NZ; 260/45.9 R; 260/45.95 F; 260/326.5 B; 260/570 R; 260/326.5 C; 544/101; 546/101
[58] Field of Search ............ 260/591, 570 R, 45.95 F, 260/45.9 R, 247.7 Z, 326.5 B, 326.5 C, 293.78, 45.8 NZ, 45.8 N

[56] References Cited

U.S. PATENT DOCUMENTS

| | | | |
|---|---|---|---|
| 2,763,657 | 9/1956 | Allen et al. | 260/570 R |
| 3,160,665 | 12/1964 | Siegrist et al. | 260/570 R |
| 3,285,912 | 11/1966 | Palopoli et al. | 260/570 R |
| 3,649,695 | 3/1972 | Millionis | 260/591 |

FOREIGN PATENT DOCUMENTS 50-74579  6/1975  Japan .

*Primary Examiner*—V. P. Hoke
*Attorney, Agent, or Firm*—Otto S. Kauder

[57] ABSTRACT

A novel process is provided for preparing 5,5'-methylenebis(2-hydroxy-4-alkoxybenzophenone), comprising forming a novel 2-hydroxy-4-alkoxy-5-aminomethylbenzophenone by a reaction of a 2-hydroxy-4-alkoxybenzophenone with an amine and formaldehyde, and causing the 2-hydroxy-4-alkoxy-5-aminomethylbenzophenone to react with a 2-hydroxy-4-alkoxybenzophenone or to dimerize.

Both the aminomethylhydroxyalkoxybenzophenone and the methylenebis (2-hydroxy-4-alkoxybenzophenone) which are prepared according to this invention are useful to prevent photo-degradation of organic materials, particularly as light stabilizers for synthetic resins.

5 Claims, No Drawings

PROCESS FOR PREPARING A 5,5'-METHYLENEBIS(2-HYDROXY-4-ALKOXYBENZOPHENONE)

BACKGROUND OF THE INVENTION

This invention relates to 2-hydroxy-4-alkoxybenzophenone ultraviolet radiation absorbing compounds, to a process for preparing such compounds, to synthetic resins stabilized against the harmful effects of ultraviolet radiation by incorporating in such resins small quantities of such compounds, and to stabilizer compositions comprising such compounds in combination with a known polymer stabilizer.

Certain 2-hydroxy-4-alkoxybenzophenone compounds are known to be effective ultraviolet absorbers and light stabilizers, with the 2-hydroxyl group critically necessary for effectiveness. These are among a large number of classes of compounds disclosed in the patent literature as meeting the requirements for an effective ultraviolet radiation absorber. In lieu of individual references, the review by G. R. Lappin in "Encyclopedia of Polymer Science and Technology" (N. Bikales, ed. New York, John Wiley-Interscience, 1971) Vol. 14, pages 125 to 148 can be consulted.

According to Lappin's review, the 18 2-hydroxybenzophenone compounds indicated to be in commercial use as stabilizers are low to moderate molecular weight compounds having a single benzophenone unit in the molecule. Lappin refers to problems of "compatibility" of the additive stabilizer with the polymer being stabilized, including such properties as the solubility of the additive in the polymer, the rate of diffusion of the additive through the polymer, and the rate of loss of the additive from the polymer. Lappin characterizes compatibility as "a sensitive function of molecular structure and not entirely predictable". Among attempts to improve on the commercially available 2-hydroxybenzophenones, Lappin indicates that longer outdoor life of polymers might be obtained with relatively high molecular weight ultraviolet radiation absorbers and states that attempts to utilize polymeric and polymerizable absorbers for this purpose had given ambiguous results and not been commercially successful.

Subsequent attempts to overcome the inadequacies of the conventional ultraviolet absorber stabilizers include a number of disclosures of 2-hydroxybenzophenones having either a plurality of benzophenone units in the molecule or functional group substitution in addition to hydroxyl and alkoxyl. Thus Lappin in U.S. Pat. No. 3,310,525 of Mar. 21, 1967 disclosed alpha-omega-bis(2-hydroxybenzoyl)alkane stabilizers for polyesters and poly-alpha-olefin resins, having a formula

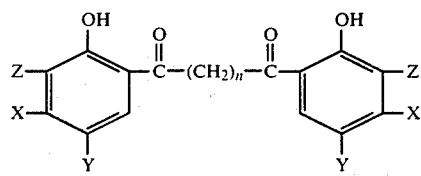

wherein n is an integer in a range from 2 to 8, and X, Y and Z are independently selected from the group of hydrogen, $C_1$-$C_4$ alkoxy and $C_1$-$C_4$ alkyl radicals.

H. Dressler in U.S. Pat. No. 3,399,237 of Aug. 27, 1968 disclosed ultraviolet light stabilizing derivatives of 4-benzoylresorcinol having the formula

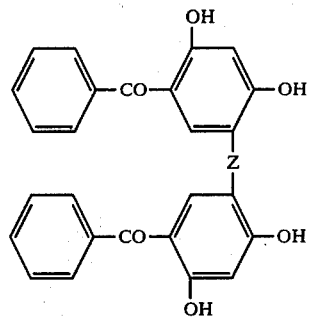

wherein Z is a member selected from the group consisting of sulfur and

and R is a member selected from the group consisting of hydrogen and alkyl having from 1-11 carbon atoms.

M. Minagawa in Japan Kokai No. 74 78,692 of July 29, 1974 disclosed 2-hydroxybenzophenone derivatives carrying cyclic imide substituents linked to the 4-position of the 2-hydroxybenzophenone by an alkyleneoxy group, for example 4-(2-phthalimidethoxy)-2-hydroxybenzophenone.

M. Minagawa in Japan Kokai No. 75 74579 of June 19, 1975 disclosed 2-hydroxybenzophenone derivatives having from 2 to 7 hydroxybenzophenone units linked through such bivalent groups as methylene, methyleneoxymethylene, cyclohexylidene, sulfide, sulfinyl, sulfonyl, alkylidene, carboxyalkylidene, and carbalkoxyalkylidene, including for example methylenebis(2-hydroxy-4-methoxybenzophenone). The location of attachment of the bivalent linking group on the 2-hydroxybenzophenone unit is nowhere specified by Minagawa.

M. Minagawa in Japan Kokai No. 75 86487 of July 11, 1975 disclosed 2-hydroxybenzophenone derivatives substituted in unsepcified ring position with N-methylene cyclic amide and N-methylene cyclic imide groups.

SUMMARY OF THE INVENTION

In accordance with this invention a 2-hydroxy-4-alkoxybenzophenone having 1 to 12 carbon atoms in the alkoxy group is caused to react with formaldehyde and an amine represented by the formula $HNR_1R_2$, in which $R_1$ and $R_2$ taken together form a 5 to 6 member heterocyclic ring free of carbonyl groups and including the nitrogen atom, or are independently hydrogen or alkyl groups having 1 to 6 carbon atoms, provided that $R_1$ and $R_2$ are not simultaneously hydrogen.

This reaction provides a novel 2-hydroxy-4-alkoxy-5-aminomethylbenzophenone represented by Formula I.

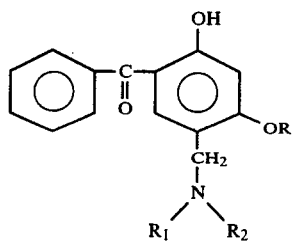

I (Formula)

in which R, $R_1$, and $R_2$ are as defined above.

The new 2-hydroxy-4-alkoxy-5-aminomethylbenzophenone is an effective stabilizer for polymers such as polyamides, polyesters both saturated and unsaturated, polyacetals, polyolefins, and polyurethanes, as well as a catalyst for the conversion of organic isocyanates to isocyanurates (i.e. trimerized isocyanates). The 2-hydroxy-4-alkoxy-5-aminomethylbenzophenone can also react, suitably in the presence of an alkaline catalyst, with a 2-hydroxy-4-alkoxybenzophenone or with itself to give a 5,5'-methylenebis(2-hydroxy-4-alkoxybenzophenone) represented by formula II which can be recovered in high yield and purity while minimizing formation of less desirable isomers and by-products. Reactions for the preparation of a new 2-hydroxy-4-alkoxy-5-aminomethylbenzophenone (reaction A) and subsequent conversion to a 5,5'-methylenebis(2-hydroxy-4-alkoxybenzophenone) (reaction B) can be written as follows:

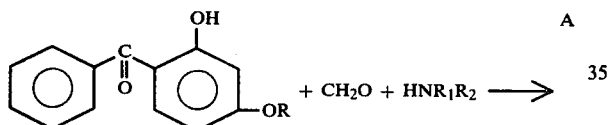

A

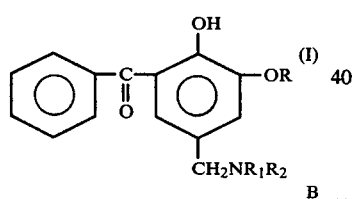

(I)

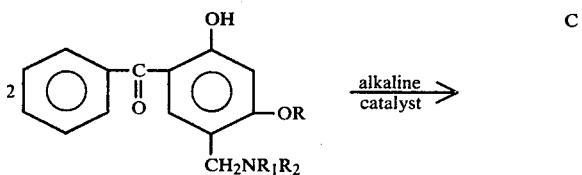

B

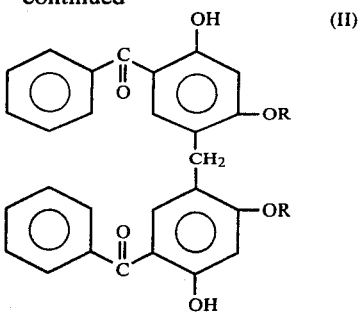

(II)

X is hydrogen or $-CH_2NR_1R_2$. Thus, when X is hydrogen, reaction B is a condensation of 2-hydroxy-4-alkoxy-5-aminomethylbenzophenone with 2-hydroxy-4-alkoxybenzophenone to give 5,5'-methylenebis(2-hydroxy-4-alkoxybenzophenone). When X is $-CH_2NR_1R_2$, the reaction can be written as a dimerization or self-condensation of 2-hydroxy-4-alkoxy-5-aminomethylbenzophenone (reaction C) to give 5,5'-methylenebis(2-hydroxy-4-alkoxybenzophenone) as follows:

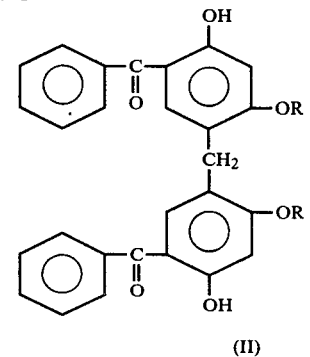

(II)

When the 2-hydroxy-4-alkoxybenzophenone used in reaction A with amine and formaldehyde to make the 2-hydroxy-4-alkoxy-5-aminomethylbenzophenone is different from the 2-hydroxy-4-alkoxybenzophenone used in the condensation reaction B with the 2-hydroxy-4-alkoxy-5-aminomethylbenzophenone to give the methylene disubstituted benzophenone product, there can be obtained in an unambiguous and selective manner an unsymmetrical bis-benzophenone of the formula:

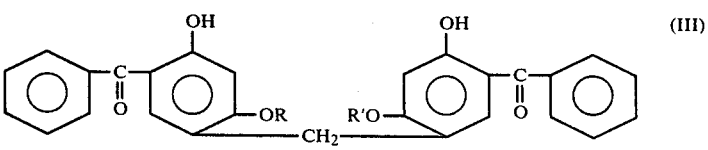

(III)

in which R and R' are dissimilar alkyl groups having 1 to 12 carbon atoms, as illustrated by the following reaction sequence using first 2-hydroxy-4-n-octoxybenzophenone in the aminomethylation reaction, followed by the condensation of the aminomethyl derivative with 2-hydroxy-4-methoxybenzophenone:

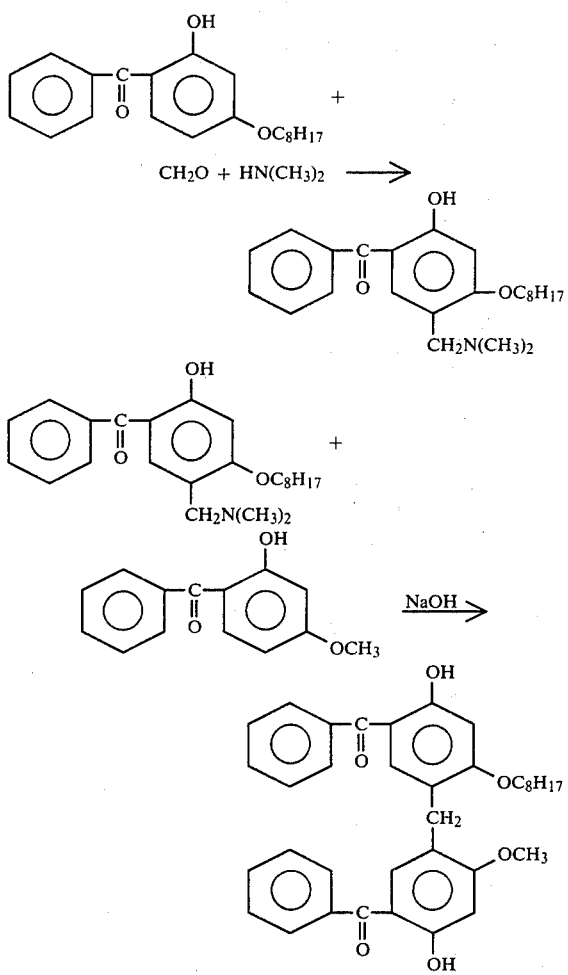

When a 2-hydroxy-4-alkoxy-5-aminomethylbenzophenone is used as a polymer stabilizer to protect a polymer against the harmful effects of light of wavelength less than 400 nanometers, effective concentrations in the polymer range from 0.01 to 1% by weight of the polymer being stabilized. Known polymer stabilizers can be used in combination with a 2-hydroxy-4-alkoxy-5-aminomethylbenzophenone of the invention in proportions of 0.1 part of known stabilizers up to 10 parts of known stabilizer per part of 2-hydroxy-4-alkoxy-5-aminomethylbenzophenone.

DESCRIPTION OF THE PREFERRED EMBODIMENTS

In formula I of the 2-hydroxy-4-alkoxy-5-aminomethylbenzophenone of this invention, R, $R_1$ and $R_2$ can be for example methyl, ethyl, propyl, isopropyl, butyl, s-butyl, isobutyl, t-butyl, amyl, isoamyl, hexyl, 2-ethylbutyl, and 4-methylpent-2-yl. In addition R can be heptyl, n-octyl, icooctyl, 2-ethylhexyl, nonyl, decyl, n-dodecyl, etc.

As examples of amines $HNR_1R_2$ used in this invention, one can cite monomethylamine, monoethylamine, monopropylamine, monobutylamine, dimethylamine, diethylamine, di-n-propylamine, diisopropylamine, di-n-butylamine, di-t-butylamine, diisobutylamine, diamylamine, ethylmethylamine, ethylisopropylamine, morpholine, pyrrolidine, and piperidine, the last three representing amines in which $R_1$ and $R_2$ taken together from a 5 to 6 member ring free of carbonyl groups.

All forms of formaldehyde can be used in the process of this invention, such as gaseous formaldehyde, aqueous solution of formaldehyde, paraformaldehyde, trioxane, tetraoxymethylene and other solid forms of formaldehyde.

The entry of the aminomethyl group in the 5 position of the 2-hydroxy-4-alkoxy-5-aminomethylbenzophenone according to this invention is unusual and unexpected, since theusual aminomethylation of phenols occurs ortho to the phenolic hydroxyl as long as an open ortho position is available.

Each stage of the process of the invention is preferably carried out in the presence of an organic solvent. Solvents that can be used in this invention preferably boil between 60° and 210° C., and include alcohols such as methanol, ethanol, isopropanol, n-butanol, 2-ethylhexanol, 2-methoxyethanol, 2-ethoxyethanol, 2-butoxyethanol, and 1-methoxy-2-propanol; aliphatic hydrocarbons such as hexane and haptane; aromatic hydrocarbons such as benzene, toluene, and xylene; hydrocarbon mixtures such as mineral spirits; and cyclic ethers such as furan, tetrahydrofuran, dioxane, and trioxane. Commercial grade solvents which can contain moisture are satisfactory for use without pretreatment. The proportion of solvent can suitably range from 5% to 5000% by weight of the combined reacting materials.

As examples of alkaline catalyst used in the process of this invention, one may cite alcoholates such as sodium methylate and sodium ethylate, also sodium hydroxide, potassium hydroxide, potassium carbonate, and sodium carbonate; any compound whose 1% aqueous solution has a pH of 10 or higher is satisfactory as an alkaline catalyst.

Each reaction stage of the process of this invention is carried out at a temperature within the range of $-10°$ C. to 200° C., preferably 20° C. to 120° C.

The proportions of reacting materials in the process of the invention are as shown in reactions A, B, and C above. Any of the reagents can be used in excess to maximize the extent of conversion of the other ingredients, particularly the relatively costly 2-hydroxy-4-alkoxybenzophenone.

The order of addition of reacting materials to the mixture is not critical and can be adjusted for the sake of convenience.

New 2-hydroxy-4-alkoxy-5-aminomethylbenzophenones represented by Formula I that can be prepared in accordance with this invention include:

2-hydroxy-4-ethoxy-5-dimethylaminomethylbenzophenone 2-hydroxy-4-isopropoxy-5-piperidinomethylbenzophenone 2-hydroxy-4-butoxy-5-diethylaminomethylbenzophenone 2-hydroxy-4-methoxy-5-morpholinomethylbenzophenone 2-hydroxy-4-n-decyloxy-5-N,N-dibutylaminomethylbenzophenone 2-hydroxy-4-n-heptoxy-5-pyrrolidinomethylbenzophenone 2-hydroxy-4-n-dodecyloxy-5-diisopropylaminomethylbenzophenone 2-hydroxy-4-isodecyloxy-5-dimethylaminomethylbenzophenone 2-hydroxy-4-methoxy-5-S-butylaminomethylbenzophenone 2-hydroxy-4-methoxy-5-N,N-di-n-hexylaminomethylbenzophenone.

5,5'-Methylenebis(2-hydroxy-4-alkoxybenzophenones) represented by formula II that can be prepared in accordance with this invention include 5,5'-methylenebis(2-hydroxy-4-methoxybenzophenone)

5,5'-methylenebis(2-hydroxy-4-ethoxybenzophenone)

5,5'-methylenebis(2-hydroxy-4-n-propoxybenzophenone)

5,5'-methylenebis(2-hydroxy-4-isobutoxybenzophenone)

5,5'-methylenebis(2-hydroxy-4-n-amyloxybenzophenone)

5,5'-methylenebis(2-hydroxy-4-(2-ethylhexyloxy)benzophenone)

5,5'-methylenebis(2-hydroxy-4-n-nonyloxybenzophenone)

5,5'-methylenebis(2-hydroxy-4-isodecyloxybenzophenone)

5,5'-methylenebis(2-hydroxy-4-n-dodecyloxybenzophenone)

as well as the following new unsymmetrical bis-benzophenones represented by formula III

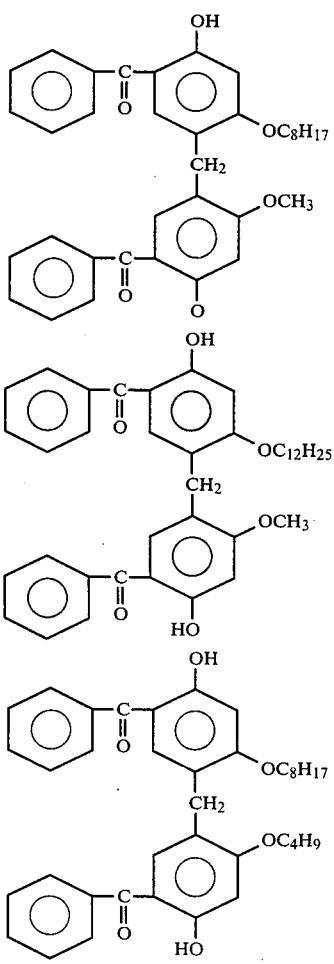

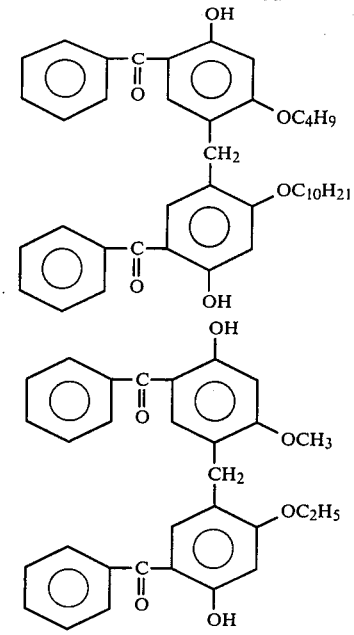

The following Examples describe the preparation of particularly preferred 2-hydroxy-4-alkoxy-5-aminomethylbenzophenones represented by Formula I and 5,5'-methylenebis(2-hydroxy-4-alkoxybenzophenones) represented by Formula II.

EXAMPLE 1

Preparation of 5-dimethylaminomethyl-2-hydroxy-4-methoxybenzophenone 228.3 g (1.0 mole) of 2-hydroxy-4-methoxy-benzophenone, 146.3 (1.3 moles, 40% aqueous solution) of dimethylamine, 105.4 g (1.3 moles, 37% aqueous solution) of formalin and 1200 ml of methanol was put into a flask, dissolved and heated under stirring at reflux temperature (68° to 70° C.) for 6 hours. When solvent was vacuum distilled off, 285 gr of 5-dimethylaminomethyl-2-hydroxy-4-methoxybenzophenone was obtained. The product had m.p. 69° C., infrared absorption at 1620 (Carbonyl), 2760 and 2800 (N—CH group) wave numbers, and neutralization equivalent (as nitrogen) 4.89% (Calculated 4.91%). The NMR spectrum provided evidence for the 5-position of the dimethylaminomethyl group.

EXAMPLE 2

Preparation of 5-dimethylaminomethyl-2-hydroxy-4-n-octoxybenzophenone 16.3 g of 2-hydroxy-4-octoxybenzophenone, 7.3 gr (40% aqueous solution) of dimethyl amine, 5.3 gr (37% aqueous solution) of formalin and 100 ml of butanol as solvent was put into a flask, dissolved and heated at 70° C. for 8 hours. After cooling, an excess of dimethyl amine, formalin, butanol and water was vacuum distilled to give a residue of 5-dimethylaminomethyl-2-hydroxy-4-n-octoxybenzophenone having m.p. 55°-62° C., infra-red absorption at 1620 (carbonyl), 2760 and 2810 (N—CH group) wave numbers, and neutralization equivalent 3.63% N (calculated 3.65%).

EXAMPLE 3

Preparation of 5-diethylaminomethyl-2-hydroxy-4-methoxybenzophenone 22.8 g of 2-hydroxy-4-methoxybenzophenone, 9.5 g of diethylamine, 10.5 g of formalin 37% solution and 30 cc of isopropanol were heated at 81.5° C. reflux for 2.5 hours then solvent was distilled off and 30.1 g of 5-diethyl aminomethyl-2-hydroxy-4-methoxybenzophenone was obtained. The product had m.p. 78°–79° C., infra-red absorption (C=O) 1630, (N—CH) 2810 wave numbers, and nitrogen 4.44% (Calc. 4.47).

EXAMPLE 4

Preparation of 5,5'-methylenebis(2-hydroxy-4-methoxybenzophenone) by catalytic dimerization 28.6 g of 5-dimethylaminomethyl-2-hydroxy-4-methoxybenzophenone, 40 ml of Pegasol 3040 (aliphatic hydrocarbon, b.p. 155° to 204° C., Mobil Chemical Co.) and 10 ml of 2-ethylhexanol was put into a flask, dissolved, added 0.5 gr of sodium methoxide and heated at 120° to 125° C. under stirring for 15 hours. After cooling, 50 ml of acetone was added and filtered. The obtained crystal was dispersed in 80 ml of water containing 0.5% acetic acid and treated at 80° C. for 3 hours.

17.5 g (yield: 74.8%) of 5,5'-methylenebis(2-hydroxy-4-methoxybenzophenone yellow crystalline fine as a powder with melting point of 229° to 230° C. was obtained after filtration and drying. The NMR spectrum provided evidence that the methylene group was attached to the 5 and 5' positions of the two 2-hydroxybenzophenone groups.

EXAMPLE 5

Preparation of 5,5'-methylenebis(2-hydroxy-4-methoxybenzophenone) from 5-dimethylaminomethyl-2-hydroxy-4-methoxybenzophenone and 2-hydroxy-4-methoxybenzophenone 14.25 gr (0.05 mole) of 5-dimethylaminomethyl-2-hydroxy-4-methoxybenzophenone, 11.4 gr (0.05 mole) of 2-hydroxy-4-methoxybenzophenone and 35 ml of n-butanol was put into a flask, dissolved, added 1 ml of sodium methoxide (28% methanol solution) and heated at reflux temperature (95° to 105° C.) under nitrogen atmosphere for 12 hours. After cooling, 30 ml of acetone was added. The precipitated product was filtered. 19.4 g (yield: 83.1%) of 5,5'-methylenebis(2-hydroxy-4-methoxybenzophenone as a yellow fine powder with melting point of 228° to 230° C. was obtained, identical with the product of Example 4 by mixed melting point and infra-red absorption spectrum.

EXAMPLE 6

Preparation of 5,5'-methylenebis(2-hydroxy-4-n-octyloxybenzophenone)

The crude 5-dimethylaminomethyl-2-hydroxy-4-n-octyloxybenzophenone obtained as described in Example 2 from 16.3 g of 2-hydroxy-4-n-octyloxybenzophenone was combined with 16.3 gr of 2-hydroxy-4-octoxybenzophenone, 1 gr of NaOH and 100 ml of xylene, then heated at 130° C. under nitrogen atmosphere for 13 hours, and then cooled, vacuum distilled to remove xylene. Toluene 200 ml was added and the mixture washed with water several times, and then dried and stripped to remove toluene.

A high viscous reaction product was obtained. Hexane was added and heated until completely dissolved, and then cooled and filtered. 23.0 g (yield: 72.5%) of 5,5'-methylenebis(2-hydroxy-4-n-octyloxybenzophenone as yellow needle crystals with meltinig point of 102° to 103° C. was obtained.

COMPARATIVE EXAMPLE 1

22.8 gr (0.1 mole) of 2-hydroxy-4-methoxybenzophenone, 6.1 gr (0.075 mole, 37% aqueous solution) of formalin and 0.6 g of conc. $H_2SO_4$ as catalyst was put into a flask and heated under stirring at reflux temperature for 13 hours. A high viscous reaction product was obtained. After cooling to room temperature, 20 ml of methanol was added, heated to remove impurities and washed with water. A yellow fine powder was obtained. The fine powder was recrystallized from toluene solution for three times, obtaining 4.7 g (yield: 19.9%) of yellow fine powder with melting point of 202° to 209° C.

COMPARATIVE EXAMPLE 2

22.8 gr (0.1 mole) of 2-hydroxy-4-methoxybenzophenone and 200 ml of dichloromethane as solvent was put into a flask, dissolved and then HCl gas was bubbled into the mixture under stirring at room temperature for 6 hours. After completion of the bubbling, the mixture was heated under stirring at 30° to 35° C. for 4 hours. The mixture was washed with water, solvent off and 20 ml of ethanol was added, heated to remove impurities. A yellow powder was obtained by retreatment with ethanol. The powder was recrystallized from toluene solution for two times, obtaining 3.1 g (yield: 13.2%) of yellow fine powder with melting point of 196° to 201° C.

It is readily seen that the use as intermediates of the 2-hydroxy-4-alkoxy-5-aminomethylbenzophenones of this invention enables the preparation of 5,5'-methylenebis(2-hydroxy-4-alkoxybenzophenones) to be carried out with greatly improved yield and purity of product.

Synthetic resins that can be stabilized with compositions comprising a 2-hydroxy-4-alkoxy-5-aminomethylbenzophenone and a known polymer stabilizer according to this invention include alphaolefin polymers such as polyethylene, polypropylene, polybutene, poly-3-methylbutene, or copolymers thereof such as ethylenevinylacetate copolymer ethylenepropylene copolymer, polystyrene, polyvinylacetate, acrylic ester resins, copolymers from styrene and another monomer (for example, maleic anhydride, butadiene, acrylonitrile and so on), acrylonitrile-butadiene-styrene copolymer; acrylic acid ester-butadiene-styrene copolymer, methacrylic acid ester-butadiene-styrene copolymer, methacrylate ester resin such as polymethylmethacrylate, polyvinylalcohol, ethylene and butylene terephthalate polyesters, polyamide, polycarbonate, polyacetal, polyurethane, cellulosic resin, or phenolic resin, urea resin, melamine resin, epoxy resin, unsaturated polyester, silicone resin, halogen-containing resins such as polyvinyl chloride, polyvinylidene chloride, polyvinylidene fluoride and copolymers thereof, and further rubbers such as isoprene rubber chloroprene rubber, and blends of the above resins.

Stabilizer compositions comprising a 2-hydroxy-4-alkoxy-5-aminomethylbenzophenone and a known polymer stabilizer according to this invention can be formulated and marketed in liquid, solid, and paste forms. An inert solvent can be used to facilitate handling. The 2-hydroxy-4-alkoxy-5-aminomethylbenzophenone and known polymer stabilizer can also be solubilized in one another by heating, such as at 70°–160° C. up to 4 hours, and then allowing the resulting melt to cool and harden sufficiently to be flaked and ground.

Known polymer stabilizers can be used in synthetic resin compositions together with the stabilizer compositions of this invention and can be admixed with the latter. Such known stabilizers include phenols, thiodipropionic acid esters, polyvalent metal salts of carboxylic acids, organic phosphites, and 1,2-epoxides.

As examples of the phenols suited for use in this invention, one may cite the following: 2,6-di-tertiarybutyl-p-cresol, stearyl-(3,5-di-methyl-4-hydroxybenzyl)-thioglycolate, stearyl-beta(4-hydroxy-3,5-di-tertiary butylphenyl) propionate, distearyl-(4-hydroxy-3-methyl-5-tertiary butyl) benzylmalonate, 2,2'-methylenebis(4-methyl-t-tertiary butylphenol), 4,4'-methylenebis(2,6-di-tertiary butylphenol), 2,2'-methylene bis(6-(1-methylcyclohexyl)-p-cresol), bis (3,3-bis(4-hydroxy-3-tertiary butylphenyl) butyric acid) glycol ester, 4,4'-butylidenebis(6-tertiary butyl-m-cresol), 1,1,3-tris(2-methyl-4-hydroxy-5-tertiary butylphenyl)-butane, 1,3,5-tris(3,5-di-tertiary butyl-4-hydroxybenzyl)-2,4,6-trimethylbenzene, tetrakis(methylene-3-(3,5-di-tertiary butyl-4-hydroxyphenyl) propionate)methane, 1,3,5-tris(3,5-ditertiary butyl-4-hydroxybenzyl)isocyanurate, 1,3,5-tris(3,5-di-tertiary butyl) 4-hydroxyphenyl) propionyloxyethyl) isocyanurate, 2-octylthio-4,6-di(4-hydroxy-3,5-di-tertiary butyl) phenoxy-1,3,5-triazine, and 4,4'-thiobis(6-tertiary butyl-m-cresol).

A comprehensive disclosure of useful phenols by M. Minagawa et al in U.S. Pat. No. 3,907,517 column 17 line 64 to column 23 line 61 is here incorporated by reference. When phenols are used, the concentration per 100 parts of polyolefin resin can range from 0.01 to about 0.5 part by weight.

Representative thiodipropionic acid esters include di-n-dodecyl thiodipropionate, dihexadecyl thiodipropionate, distearyl thiodipropionate, n-octyl eicosanyl thiodipropionate and n-octadecyl cyclohexane-1,4-dimethanol thiodipropionate polyester. A comprehensive disclosure of useful thiodipropionate esters by M. Minagawa et al in U.S. Pat. No. 3,869,423, column 17 line 55 to column 19 line 54 is here incorporated by reference.

Representative polyvalent metal salts include zinc, calcium, magnesium, barium, strontium and nickel salts of monocarboxylic acids having 6 to 24 carbon atoms, for example zinc benzoate, calcium palmitate, and nickel 2-ethylbutyrate. A comprehensive disclosure of useful metal salts by M. Minagawa et al in U.S. Pat. No. 3,869,423, column 19 line 56 to column 20 line 35 is here incorporated by reference.

Representative organic phosphites include triisodecylphosphite, tris (nonylphenyl phosphite), and 4,4'-isopropylidene diphenol $C_{12}$–$C_{15}$ mixed alkyl phosphite. A comprehensive disclosure of useful organic phosphites by M. Minagawa et al in U.S. Pat. No. 3,849,370 Column 13 line 63 to column 16 line 48 is here incorporated by reference.

Representative 1,2-epoxides include epoxysoybean oil, epoxylinseed oil, and 2-ethylhexyl epoxystearate. A comprehensive disclosure of 1,2-epoxides by M. Minagawa et al in U.S. Pat. No. 3,869,423 column 26 line 13 to line 39 is here incorporated by reference.

The preparation of the stabilized resin composition is easily accomplished by conventional procedures. A heated two roll mill, for example, is a convenient compounding tool for blending stabilizer compositions of the invention with polyolefins, vinyl chloride polymers, ABS polymers, ethylene-vinyl acetate copolymers and others.

The following Examples illustrate the use of polymer stabilizer compositions of the invention.

EXAMPLE 7

A premix of polybutylene terephthalate, 100 parts, tris-nOnylphenylphosphite 0.1 part, and 2-hydroxy-4-methoxy-5-dimethylaminomethylbenzophenone 0.25 part was processed by injection molding at 270° C. to preparedumbell speciments. Using these specimens, retention of tensile strength after 500 hours in radiation was measured.

The retention of tensile strength of this composition was greater than that of a control composition omitting the 2-hydroxy-4-methoxy-5-dimethylaminomethylbenzophenone.

EXAMPLE 8

A compound of ABS resin, 100 parts, zinc stearate 0.5 parts, 4,4'-thiobis(2-t-butyl-5-methylphenol) 0.2 part and 5-diethylaminomethyl-2-hydroxy-4-methoxybenzophenone was milled and molded to obtain a sheet 3 mm thick. On portions of this sheet the tensile strength before and after irradiation for 800 hours in the weatherometer was measured.

The above composition had superior retention of tensile strength compared to a control composition lacking the 5-diethylaminomethyl-2-hydroxy-4-methoxybenzophenone of this invention.

EXAMPLE 9

A compound of high density polyethylene 100 parts by weight, calcium stearate 0.3 parts, distearyl thiodipropionate 0.2 part and 2-hydroxy-4-n-octoxy-5-dimethylaminomethylbenzophenone 0.1 part was milled and compression molded to give a sheet 0.5 mm thick. Portions of the sheet were exposed to the radiation of a weatherometer until embrittled.

The above composition outlasted a control composition made without the 2-hydroxy-4-octoxy-5-dimethylaminomethylbenzophenone.

We claim:

1. A process for preparing 5,5'-methylene bis(2-hydroxy-4-alkoxybenzophenone) represented by the formula:

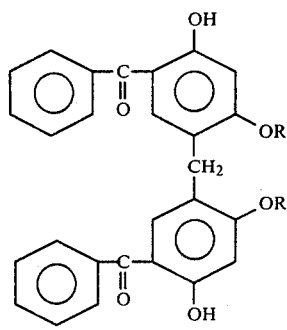

in which R is an alkyl group having 1 to 12 carbon atoms, comprising the steps of treating a 2-hydroxy-4-alkoxy-5-aminomethylbenzophenone represented by the formula

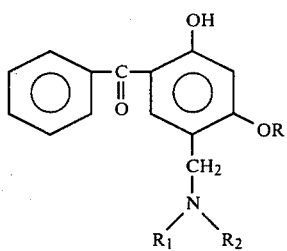

in which R is an alkyl group having 1 to 12 carbon atoms, and $R_1$ and $R_2$ taken together form a 5 to 6 member heterocyclic ring free of carbonyl substituents and including the nitrogen atom, or are independently hydrogen atoms or alkyl groups having 1 to 6 carbon atoms, provided that $R_1$ and $R_2$ are not simultaneously hydrogen, with a 2-hydroxy-4-alkoxybenzophenone represented by the formula

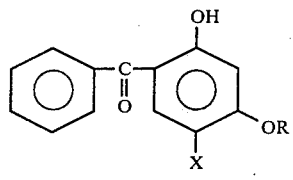

in which R is an alkyl group having 1 to 12 carbon atoms and X is hydrogen or —$CH_2NR_1R_2$ in the presence of alkali and an organic solvent, removing the solvent, and recovering the 5,5'-methylenebis-(2-hydroxy-4-alkoxybenzophenone).

2. A process according to claim 1 in which X is hydrogen.

3. A process according to claim 1 in which X is —$CH_2N(CH_3)_2$.

4. A process according to claim 1 in which the solvent is a hydrocarbon having a boiling point of 60° to 210° C.

5. A process according to claim 1 in which the solvent is an alcohol having a boiling point between 60° and 210° C.

* * * * *